United States Patent [19]
Van Eden et al.

[11] Patent Number: 5,268,170
[45] Date of Patent: Dec. 7, 1993

[54] METHODS OF TREATMENT AND DIAGNOSIS OF AUTOIMMUNE DISEASES, ESPECIALLY ARTHRITIC CONDITIONS

[75] Inventors: Willem Van Eden, Bilthoven; Jelle E. R. Thole, Diemen; Johannes D. A. Van Embden, Utrecht; Ruurd Van Der Zee, Groningen, all of Netherlands; Irun R. Cohen, Rehovot, Israel

[73] Assignee: YEDA Research and Development Co., Ltd., Rehovot, Israel

[21] Appl. No.: 946,818

[22] Filed: Sep. 17, 1992

Related U.S. Application Data

[63] Continuation of Ser. No. 094,663, Sep. 9, 1987, abandoned.

[30] Foreign Application Priority Data

Sep. 9, 1986 [NL] Netherlands .......................... 8602270
May 14, 1987 [NL] Netherlands .......................... 8701163

[51] Int. Cl.$^5$ ..................... A61K 39/04; A61K 39/02
[52] U.S. Cl. .......................................... 424/92; 424/88
[58] Field of Search ................................. 424/88, 92

[56] References Cited

FOREIGN PATENT DOCUMENTS 8505034 11/1985 World Int. Prop. O. .

OTHER PUBLICATIONS

Infection and Immunity, vol. 50. 50, No. 3, Dec. 1985, pp. 800–806, American Society for Microbiology, WA., US.

J. E. R. Thole et al.: "Cloning of Mycobacterium bovis BCG DNA and expression of antigens in *Escherichia coli*".

(List continued on next page.)

*Primary Examiner*—Christine M. Nucker
*Assistant Examiner*—H. Sidberry
*Attorney, Agent, or Firm*—Brumbaugh, Graves, Donohue & Raymond

[57] ABSTRACT

A *Mycobacterium bovis* BCG polypeptide having a molecular mass of about 64 kD was found to be useful as an immunogen inducing resistance to autoimmune arthritis and similar autoimmune diseases.

The invention relates to methods of treatment and diagnosis of autoimmune diseases especially arthritic conditions, in which said polypeptide is used.

The invention also relates to a polypeptide comprising the epitope essential for this activity. The polypeptide has the formula

```
171           181           191
GVITVEESNT    FGLQLELTEG    MRFDKGYISG 201           211           221
YFVTDPERQE    AVLEDPYILL    VSSKVSTVKD

231
LLPLLEKVIG.
```

Further, the invention relates to polypeptides showing sequential homology with said polypeptide, and to derivatives and multimers thereof. Also, microorganisms expressing the polypeptides either as such or as part of a fusion protein or as a multimer, form part of the invention.

Finally, the invention relates to pharmaceutical compositions, diagnostic compositions and test kits comprising a compound according to the invention.

6 Claims, No Drawings

OTHER PUBLICATIONS

Young et al.: "Dissection of Mycobacterium tuberculosis antigens using recombinant DNA".

Chemical Abstracts, vol. 105, No. 17, Oct. 27, 1986, p. 525, Abstract No. 151096y, Columbus, OH, US; W. J. Britton et al.

"Immunoreactivity of a 70 kD protein purified from Mycobacterium bovis Bacillus Calmette-Guerin by monoclonal antibody affinity chromatography", and J. Exp. Med. 1986, 164(3), 695-708. Abs.

Proc. Natl. Acad. Sci. vol. 82, May 1985, pp. 2583-2587; R. A.

The Etiologic Agents of Leprosy and Tuberculosis Share an Immunoreactive Protein Antigen with the Vaccine Strain Mycobacterium Bovis BCG, Inf. Immunity, 55:1932-1935, Shinnick, et al.

A Recombinant 64 Kilodalton Protein of Mycobacterium Bovis Bacillus Calmette-Guerin Specifically Stimulates Human T4 Clones Reactive to Mycobacterial Antigens, J. Exp. Med. 163:1024-1029 (1986), Emmrich et al.

Evidence for an HLA-DR4-Associated Immune-Response Gene For Mycobacterium Tuberculosis, The Lancet, 2:310-313, 1986, Ottenhoff.

Characterization, Sequence Determination and Immunogenicity of a 64-Kilodalton Protein of Mycobacterium Bovis BCG Expressed in *Escherichia Coli* K-12, Inf. Immunity, 55:1466-1475 (1987) Thole et al.

METHODS OF TREATMENT AND DIAGNOSIS OF AUTOIMMUNE DISEASES, ESPECIALLY ARTHRITIC CONDITIONS

This application is a continuation of application Ser. No. 07/094,663, filed on Sep. 9, 1987 now abandoned.

The present invention relates to a method of prophylaxis and treatment, and a method of diagnosis of autoimmune diseases, especially arthritic conditions. The invention further relates to a new peptide and compounds related to said peptide, to micro-organisms expressing said peptide and related compounds, and to pharmaceutical and diagnostic compositions comprising the new peptide or a compound related to said peptide, and to test kits for performing immunological tests.

BACKGROUND OF THE INVENTION

Millions of persons are afflicted with chronic forms of arthritis which are thought to involve autoimmunity to constituents of the joints or connecting tissues of the body. These conditions include rheumatoid arthritis, ankylosing spondylitis, Reiter's syndrome and other forms of reactive arthritis. The etiology of these diseases is not known, but previous infection with various microbes seems to act as an inciting circumstance in genetically susceptible individuals. For example, patients with rheumatoid arthritis may show unusual reactivity to mycobacterial antigens and immunization with the BCG strain of mycobacteria was found to lead to arthritis in 15 of 150 individuals. Ankylosing spondylitis has been associated with infection by Klebsiella or Yersinia species of bacteria and other cases of arthritis by Salmonella, Shigella, etc. There is no evidence of active infection of joints by these microbes in the vast majority of cases and it has been postulated that microbial infection may trigger an aberrant, autoimmune response of the individual against his own antigens present in the joints. Adjuvant arthritis (AA) is an experimental model of arthritis inducible by immunizing susceptible strains of rats to Mycobacteria. The disease which develops about 12 days after immunization has many of the features of rheumatoid arthritis and AA has been considered to be a model of rheumatoid arthritis.

PRIOR ART

EP A 0 181 364 discloses aqueous acetone soluble and insoluble fractions of certain mycobacteria, such as Mycobacterium H-37, M. kansasii and M. vaccae. The soluble fraction of Myc. H-37 was found to provoke an immune response leading to resistance to adjuvant arthritis. The insoluble fraction seemed to be responsible for induction of adjuvant arthritis. Micobacterium vaccae was shown to be substantially free of adjuvant arthritis inducing components. Further, EP A 0 181 364 describes certain lines and clones of T-lymphocytes selected for their reactivity to micobacteria. These can be used for producing arthritis upon inoculation into irradiated rats. One line, designated as A2 was found to induce arthritis upon intravenous injection into irradiated rats. The same line, A2 is effective in vaccinating unirradiated rats against subsequent autoimmune arthritis induced by active immunization to mycobacteria. Cell line A2 has been cloned. There were obtained two distinct clones, designated as A2b and A2c, respectively. A2b causes arthritis but does not vaccinate against it; clone A2c does not cause arthritis but vaccinates against it. In addition to preventing arthritis, clone A2c can be used to treat AA. Moreover, clones A2b and A2c can be used to identify antigens associated with arthritogenicity or with suppression of arthritogenicity. Both clones respond to whole mycobacteria as well as to cartilage proteoglycan.

DESCRIPTION OF THE INVENTION

According to the present invention it was found that a polypeptide having a molecular mass of about 64 kD, the preparation of which is described in Infection and Immunity 1985, pages 800-806, is useful as an immunogen inducing resistance to autoimmune arthritis and similar autoimmune diseases.

In the above-mentioned article the peptide in question is called Antigen A and this designation will be used here as well. Antigen A was obtained by constructing a gene bank of Mycobacterium bovis BCG DNA in Escherichia coli by cloning Sau3A-cleaved mycobacterium DNA fragments into the lambda vector EMBL3. The expression of mycobacterial antigens was analyzed by Western blotting with hyperimmune rabbit sera. The article states that among 770 clones tested, several were found that produced various mycobacterial antigens in low amounts, with concentrations generally close to the detection limit. One particular clone was chosen for further investigation. This clone produced a 64 kD antigen. By placing the lambda promoter $P_L$ in front of the structural gene of this antigen, an overproducing E. coli strain was obtained. The article shows that antigens cross-reacting with the 64 kD protein are present in a wide variety of mycobacteria and also in so-called purified protein derivatives which are routinely used for skin tests. Finally, it is stated in the article that preliminary experiments indicate the presence of antibodies against the 64 kD antigen in sera from tuberculosis patients.

According to the present invention, Antigen A was found to have the following amino acid sequence:

| 1 | MAKTIAYDEE | ARRGLERGLN | ALADAVKVTL |
|---|---|---|---|
| 61 | LEDPYEKIGA | ELVKEVAKKT | DDVAGDGTTT |
| 121 | KAVEKVTETL | LKGAKEVETK | EQIAATAAIS |
| 181 | FGLQLELTEG | MRFDKGYISG | YFVTDPERQE |
| 241 | AGKPLLIIAE | DVEGEALSTL | VVNKIRGTFK |
| 301 | EEVGLTLENA | DLSLLGKARK | VVVTKDETTI |
| 361 | EKLQERLAKL | AGGVAVIKAG | AATEVELKER |
| 421 | APTLDELKLE | GDEATGANIV | KVALEAPLKQ |
| 481 | VYEDLLAAGV | ADPVKVTRSA | LQNAASIAGL |
| 1 | GPKGRNVVLE | KKWGAPTITN | DGVSIAKEIE |
| 61 | ATVLAQALVR | EGLRNVAGA | NPLGLKRGIE |
| 121 | AGDQSIGDLI | AEAMDKVGNE | GVITVEESNT |
| 181 | AVLEDPYILL | VSSKVSTVKD | LLPLLEKVIG |
| 241 | SVAVKAPGFG | DRRKAMLQDM | AILTGGQVIS |
| 301 | VEGAGDTDAI | AGRVAQIRQE | IENSDSDYDR |
| 361 | KHRIEDAVRN | AKAAVEEGIV | AGGGVTLLQA |
| 421 | IAFNSGLEPG | VVAEKVRNLP | AGHGLNAQTG |
| 481 | FLTTEAVVAD | KPEKEKASVP | GGGDMGGMDF |

DETAILED DISCUSSION OF THE INVENTION

As mentioned above clones A2b and A2c as disclosed in EP A 0 181 364 can be used to identify antigens associated with arthritogenicity or with suppression of arthritogenicity. Both clones respond to whole mycobacteria and both A2b and A2c respond to antigen A.

T-cell clones A2b, A2c and control cell-line C1a (anti-ovalbumin) were assayed for in vitro proliferative responses to *Micobacterium tuberculosis*, Antigen A, *E. coli* control lysate, ovalbumin (OVA) and mitogen ConA in a standard test ($20 \times 10^3$ clone/line cells, $2 \times 10^6$ irradiated accessory cells and antigens in optimum concentrations per well, $^3$H-Thymidine incorporation for 18 hours after 48 hours of incubation). The following table A shows the test results which are expressed as stimulation indexes.

TABLE A

|  | M. tub. | Ant. A | coli contr. | OVA | ConA |
|---|---|---|---|---|---|
| A2b | 180 | 500 | 2.9 | — | 430 |
| A2c | 304 | 516 | 1.5 | — | 390 |
| C1a | — | 1.5 | 1.2 | 45 | 64 |

The in vivo potency of Antigen A was checked by immunizing rats with Antigen A before and after induction of arthritis with *M. tuberculosis*. The test with challenge after immunization was carried out as follows:

Groups of 4 Lewis rats were treated by intraperitoneal inoculation of water, Antigen A (50 µg) and *E. coli* control lysate (amount equivalent to coli content of 50 µg Antigen A) in oil. 35 Days later, susceptibility to induction of adjuvant arthritis was tested by inoculating the rats intracutaneously with *M. tuberculosis* (1 mg) in oil. Occurrence of arthritis was checked by daily inspection of the rat joints. The results are shown in table B.

TABLE B

| Primary immunization | | Secondary challenge (35 days later) with *M. tuberculosis* in oil. | |
|---|---|---|---|
| Inoculum in oil | Arthritis incidence | Arthritis incidence | Clinical grade |
| Water | 0/4 | 4/4 | severe |
| Antigen A | 0/4 | 2/4 | very mild |
| *E. coli* contr. | 0/4 | 4/4 | severe |

The tests involving inoculation after induction of autoimmune arthritis were carried out as follows:

Arthritis was induced by inoculating groups of 3 Lewis rats with *M. tuberculosis* (1 mg) in oil intracutaneously. 3 Days later the rats were treated by intraperitoneal inoculation of water, Antigen A (200 µg) and *E. coli* control lysate (amount equivalent to coli content of 200 µg Antigen A) in oil. Occurrence of arthritis was checked by daily inspection of the rat joints. The results are shown in table C.

TABLE C

| Inoculum administered at | Arthritis | |
|---|---|---|
| day 3 after disease induction | incidence | clinical grade |
| Water | 3/3 | severe |
| Antigen A | ¾ | very mild |

TABLE C-continued

| Inoculum administered at | Arthritis | |
|---|---|---|
| day 3 after disease induction | incidence | clinical grade |
| *E. coli* contr. | 3/3 | severe |

It is seen that Antigen A is not arthritogenic by itself but reduces the incidence of arthritis after active induction disease with 50%, and also reduces the severity of remaining disease remarkably. A similar reduction of disease incidence and severity is seen when Antigen A is administered three days after disease is induced. *E. coli* itself has no effect. Thus, Antigen A is arthritis suppressive, while not being arthritogenic.

Further, it was found that Antigen A cross-reacts with similar proteins present in various other mycobacteria and *E. coli* and with Treponema and gram-negative enterobacteria. This cross-reactivity is shown in the following table D.

TABLE D

Cross-reactivity between Antigen A and antigens present in other bacteria.

|  | Antig. A | 64kD of mycobact. | *E. coli* 60kD | Trep. poll | Shig. | Salmon. | Klebsiella |
|---|---|---|---|---|---|---|---|
| MCA HATR |  |  |  |  |  |  |  |
| 1-24 | + | — | + | + | + | + | + |
| F47-10 | + | + | + |  | + | + | + |
| Polycl. anti comm. ag. Legion/ Pseudom. | + | + | + | + | + | + | + |

Serological cross-reactivity as shown by Western-blot analysis. HATR 1-24 and F47-10 are monoclonal antibodies raised against Treponema and *Mycobacterium tuberculosis* respectively. The polyclonal serum was raised against the common antigen of Legionella and Pseudomonas.

This indicates that epitopes present on Antigen A are similarly present on presumably equivalent proteins of various bacterium species, such as from Mycobacterium, Escherichia, Treponema, Shigella, Salmonella, Yersinia, Nocardia, Campylobacter, or Klebsiella species. Particularly, antigen A amino acid sequence 190-213 is also present in a corresponding 65 KD protein from *Mycobacterium leprea*, with the exception that, in the *M. leprae* protein, amino acid 206 is not proline, but alanine.

Further, it was found that only part of the Antigen A sequence is responsible for the stimulating activity upon T-cell clones A2b and A2c. This was determined by testing Antigen A fragments, namely truncated derivatives produced by deletion mutants of the gene, fusion proteins with β-galactosidase and proteolysis products of Antigen A, for their ability to stimulate said T-cell clones. These fragments were obtained by means of recombinant-DNA techniques, by incorporating parts of the Antigen A gene, in some cases fused to the β-galactosidase gene, into a plasmide and expressing in *E. coli* K12 M1070.

The peptide with Antigen A amino acid sequence 234-540 was shown not to stimulate clones A2b and A2c. However, the fragment lacking amino acid sequence 481-540 did. β-Galactosidase-fused peptides with Antigen A amino acid sequences 61-540, 109-540 and 171-540 were reactive, those with amino acid sequences 272-540 and 280-540 were not reactive. β-Galactosidase alone was not reactive.

Therefore, the epitope responsible for the stimulation of T-cell clones A2b and A2c resides in amino acid sequence 171-234.

In order to further characterize the area which is essential for the T-cell epitopes, protease digests of Antigen A were tested for their stimulating activity on both T-cell clones. Digesting Antigen A with clostripain yielded only one reactive mixture of two peptides. The mixture is called CP15. The two peptides, which were not separated, are designated as CP15a and CP 15b. The CP15a sequence begins with amino acid 193 and that of CP15b starts with amino acid 197. Digesting CP15 with trypsin, again, yielded a reactive mixture of two peptides (CP-TP-T12a and b) with sequences beginning with amino acid 193, and 196, respectively, as well as a non-reactive peptide, the sequence of which starts with amino acid 209. The carboxy ends of the peptides were not determined.

It may be concluded from these results that the epitope responsible for the stimulation of T-cell clones A2b and A2c resides in Antigen A amino acid sequence 193-234, and more specifically in the amino acid sequence 193-208.

and the occurrence of any reaction is detected by means of immunological methods known per se.

In the in vivo skin test the skin reaction at the site of the injection is measured after a sufficient time period, for example 24 to 72 hours after administration. Swelling and/or redness is due to a delayed hypersensitivity-like reaction.

In the in vitro tests with blood or blood components, Antigen A may be contacted, for example, with peripheral blood cells. Lymphocytes of positive patients will be stimulated by Antigen A in that they will proliferate and/or produce biologically active factors, such as interleukines or products involved in the degradation of cartilage. Such reactions may be detected by methods known in the art.

In in vitro serological tests serum of a patient is contacted with Antigen A. If the serum contains antibodies against antigenic determinants of Antigen A an immunological reaction will occur which may be detected and assayed by means of standard techniques such as ELISA, agglutination, etc.

The invention also relates to the polypeptide having Antigen A amino acid sequence 171-240 which is

| 171 | 181 | 191 | 201 |
|---|---|---|---|
| GVITVEESNT | FGLQLELTEG | MRFDKGYISG | YFVIDPERQE |
| 211 | 221 | 231 | |
| AVLEDPYILL | VSSKVSTVKD | LLPLLEKVIG, | |

Finally, it was found that a synthetic peptide having Antigen A amino acid sequence 180-196 is also recognized by T-cell clones A2b and A2c. The overlap between this synthetic peptide and the above-discussed digests is only 4 amino acids, namely Antigen A amino acids 193-196 designated as FDKG. Therefore, at least one of these amino acids seems to be essential in the T-cell epitope. It is possible that one or more of these amino acids is seen by the T-cells in conjunction with additional amino acids having lower or higher numbers or lower and higher numbers in the sequence. Therefore, the polypeptide having Antigen A amino acid sequence 171-240, and polypeptides showing sequential homology with this peptide will comprise the epitope of T-cell clones A2b and A2c. In this specification, polypeptides showing sequential homology with the polypeptide having Antigen A amino acid sequence 171-240 are polypeptides composed of 4 to 70 amino acid residues, in the amino acid sequence of which at least 4 amino acid residues are in the same relative position as the same amino acid residues are in the polypeptide having Antigen A amino acid sequence 171-240.

Consequently, the invention relates to a method of prophylaxis or treatment of autoimmune diseases, especially arthritic conditions, in which an effective amount of Antigen A, that is the polypeptide having the sequence of 540 amino acids mentioned earlier in this specification, is administered to a patient.

Preferably, Antigen A is administered orally, intracutaneously or intramuscularly in the form of a suitable pharmaceutical composition which may be prepared in a way known in the art.

Further, the invention relates to a method for the diagnosis of autoimmune diseases, especially arthritic conditions in which Antigen A is injected intracutaneously into a patient, and the occurrence of a detectable skin reaction is observed, or in which Antigen A is contacted with a patient's blood or blood component, as well as to polypeptides composed of 4-70 amino acid residues, and showing sequential homology with said polypeptide having Antigen A amino acid sequence 171-240 in the sense that in its amino acid sequence at least 4 of the amino acid residues are in the same relative position as the same amino acid residues are in the polypeptide having Antigen A amino acid sequence 171-240.

More specifically, the invention relates to polypeptides showing sequential homology with the polypeptide having Antigen A amino acid sequence 171-240, which are further characterized by the fact that they comprise in their amino acid sequence at least one of amino acid residues F, D, K and G corresponding to positions 193, 194, 195 and 196. Preferably, these polypeptides comprise in their molecule amino acid sequences 193-234, 193-208 or 180-196.

Although T-cell clones A2b and A2c respond to all of the above-defined polypeptides, the antigenicity and immunogenicity of the polypeptides may be enhanced by coupling thereto at least one radical capable of improving the presentation of the antigenic determinants of the polypeptides. Such radicals are known in the art, and comprise, for example, radicals of peptides, tetanus toxoid, diphtheria toxoid, $\beta$-galactosidase, and microbial outer membrane proteins. Multimers of the polypeptides in question are also contemplated. These modified polypeptides also form part of the invention.

All of the polypeptides of the invention, namely the polypeptide having Antigen A amino acid sequence 171-240, the polypeptides showing sequential homology with that polypeptide, the above-defined modified peptides including the multimers, can be used as immunogens in pharmaceutical compositions, especially vaccines for the alleviation and treatment of autoimmune diseases, especially arthritic conditions, and also as antigens in diagnostic compositions for the diagnosis of these diseases. These pharmaceutical and diagnostic compositions, which may be prepared in a way known in the art, also form part of the invention.

Another way to improve the immunogenicity of the polypeptides according to the invention is to construct, by known genetical engineering methods, microorganisms expressing a polypeptide according to the invention either as such or as part of a fusion protein or as a multimer thereof. These microorganisms can be used for the preparation of a live vaccine which will provoke not only the production of antibodies against the microorganism in question, but will also be useful for the alleviation and treatment of autoimmune diseases. These genetically engineered microorganisms, and pharmaceutical compositions containing these, also form part of the invention. Examples of suitable genetically engineered microorganisms are Vaccinia and Salmonella strains.

Finally, the invention provides kits for performing immunological tests comprising a container with at least one of the antigenic compounds discussed above, or a container with the diagnostic composition mentioned above.

The antigenic compounds and diagnostic compositions as well as the diagnostic kits according to the invention may be used for various types of assays, such as:

a.1. a lymphocyte proliferation test, or determination of any entity indicative of such proliferation;

a.2. indicative of the measure of lymphocyte activation are also changes which can be assayed by standard means so as to establish the presence and degree of lymphocyte activation: amongst these there may be mentioned:

a. production of lymphokines (such as interleukin-2 (IL-2));
  b. gamma interferon;
  c. migration inhibition factor (MIF);
  d. expression of membrane markers, such as IL-2 receptor; peanut agglutination receptor;
  e. expression of enzymes such as heparanase.

b. determination of antibody titer in absolute terms or as a ratio of the values obtained by different compositions, said values or ratios being indicative of the presence or absence of the disease. Quantitative values obtained are of use in establishing the severity of the disease.

The diagnostic compositions according to the invention may be prepared by combining one or more antigenic compounds according to the invention as above-defined with suitable adjuvants and auxiliary components. Standardized kits with reference and calibration means are of value in the rapid and convenient determination of arthritic disease and its stage and/or severity.

We claim:

1. A method for the prophylaxis or treatment of arthritis-type autoimmune diseases comprising administering to a patient a therapeutically effective amount of a 64 kilodalton polypeptide having the formula

| 1 | MAKTIAYDEE | ARRGLERGLN | ALADAVKVTL |
| 61 | LEDPYEKIGA | ELVKEVAKKT | DDVAGDGTTT |
| 121 | KAVEKVTETL | LKGAKEVETK | EQIAATAAIS |
| 181 | FGLQLELTEG | MRFDKGYISG | YFVTDPERQE |
| 241 | AGKPLLIIAE | DVEGEALSTL | VVNKIRGTFK |
| 301 | EEVGLTLENA | DLSLLGKARK | VVVTKDETTI |
| 361 | EKLQERLAKL | AGGVAVIKAG | AATEVELKER |
| 421 | APTLDELKLE | GDEATGANIV | KVALEAPLKQ |
| 481 | VYEDLLAAGV | ADPVKVTRSA | LQNAASIAGL |

| 1 | GPKGRNVVLE | KKWGAPTITN | DGVSIAKEIE |
| 61 | ATVLAQALVR | EGLRNVAGA | NPLGLKRGIE |
| 121 | AGDQSIGDLI | AEAMDKVGNE | GVITVEESNT |
| 181 | AVLEDPYILL | VSSKVSTVKD | LLPLLEKVIG |
| 241 | SVAVKAPGFG | DRRKAMLQDM | AILTGGQVIS |
| 301 | VEGAGDTDAI | AGRVAQIRQE | IENSDSDYDR |
| 361 | KHRIEDAVRN | AKAAVEEGIV | AGGGVTLLQA |
| 421 | IAFNSGLEPG | VVAEKVRNLP | AGHGLNAQTG |
| 481 | FLTTEAVVAD | KPEKEKASVP | GGGDMGGMDF |

2. A method according to claim 1, wherein the polypeptide is prepared by recombinant techniques.

3. A method for the diagnosis of arthritis-type autoimmune diseases in a patient comprising intracutaneously administering to the patient a 64 kilodalton polypeptide having the formula

| 1 | MAKTIAYDEE | ARRGLERGLN | ALADAVKVTL |
| 61 | LEDPYEKIGA | ELVKEVAKKT | DDVAGDGTTT |
| 121 | KAVEKVTETL | LKGAKEVETK | EQIAATAAIS |
| 181 | FGLQLELTEG | MRFDKGYISG | YFVTDPERQE |
| 241 | AGKPLLIIAE | DVEGEALSTL | VVNKIRGTFK |
| 301 | EEVGLTLENA | DLSLLGKARK | VVVTKDETTI |
| 361 | EKLQERLAKL | AGGVAVIKAG | AATEVELKER |
| 421 | APTLDELKLE | GDEATGANIV | KVALEAPLKQ |
| 481 | VYEDLLAAGV | ADPVKVTRSA | LQNAASIAGL |

| 1 | GPKGRNVVLE | KKWGAPTITN | DGVSIAKEIE |
| 61 | ATVLAQALVR | EGLRNVAGA | NPLGLKRGIE |
| 121 | AGDQSIGDLI | AEAMDKVGNE | GVITVEESNT |
| 181 | AVLEDPYILL | VSSKVSTVKD | LLPLLEKVIG |
| 241 | SVAVKAPGFG | DRRKAMLQDM | AILTGGQVIS |
| 301 | VEGAGDTDAI | AGRVAQIRQE | IENSDSDYDR |
| 361 | KHRIEDAVRN | AKAAVEEGIV | AGGGVTLLQA |
| 421 | IAFNSGLEPG | VVAEKVRNLP | AGHGLNAQTG |
| 481 | FLTTEAVVAD | KPEKEKASVP | GGGDMGGMDF | and observing for the presence of a detectable skin reaction.

4. A method according to claim 3, wherein the polypeptide is prepared by recombinant techniques.

5. A method for the diagnosis of arthritis-type autoimmune diseases in a patient comprising combining a 64 kilodalton polypeptide having the formula

| 1 | MAKTIAYDEE | ARRGLERGLN | ALADAVKVTL |
| 61 | LEDPYEKIGA | ELVKEVAKKT | DDVAGDGTTT |
| 121 | KAVEKVTETL | LKGAKEVETK | EQIAATAAIS |
| 181 | FGLQLELTEG | MRFDKGYISG | YFVTDPERQE |
| 241 | AGKPLLIIAE | DVEGEALSTL | VVNKIRGTFK |
| 301 | EEVGLTLENA | DLSLLGKARK | VVVTKDETTI |
| 361 | EKLQERLAKL | AGGVAVIKAG | AATEVELKER |
| 421 | APTLDELKLE | GDEATGANIV | KVALEAPLKQ |
| 481 | VYEDLLAAGV | ADPVKVTRSA | LQNAASIAGL |

| 1 | GPKGRNVVLE | KKWGAPTITN | DGVSIAKEIE |
| 61 | ATVLAQALVR | EGLRNVAGA | NPLGLKRGIE |
| 121 | AGDQSIGDLI | AEAMDKVGNE | GVITVEESNT |
| 181 | AVLEDPYILL | VSSKVSTVKD | LLPLLEKVIG |
| 241 | SVAVKAPGFG | DRRKAMLQDM | AILTGGQVIS |
| 301 | VEGAGDTDAI | AGRVAQIRQE | IENSDSDYDR |
| 361 | KHRIEDAVRN | AKAAVEEGIV | AGGGVTLLQA |
| 421 | IAFNSGLEPG | VVAEKVRNLP | AGHGLNAQTG |
| 481 | FLTTEAVVAD | KPEKEKASVP | GGGDMGGMDF | with a sample of the patient's blood or an immunologically complete fraction thereof and monitoring the combined sample for the occurrence of an immunological reaction.

6. A method according to claim 5, wherein the polypeptide is prepared by recombinant techniques.

* * * * *